(12) United States Patent
Iomantas et al.

(10) Patent No.: US 6,350,596 B2
(45) Date of Patent: Feb. 26, 2002

(54) METHOD FOR PRODUCING L-PHENYLALANINE

(75) Inventors: Yurgis Antanas Vladovich Iomantas; Elena Georgievna Abalakina, both of Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/791,707

(22) Filed: Feb. 26, 2001

(30) Foreign Application Priority Data

Mar. 3, 2000 (RU) ........................................ 2000105201

(51) Int. Cl.$^7$ ................................................ C12P 13/22
(52) U.S. Cl. ................ 435/108; 435/252.31; 435/252.5
(58) Field of Search .............................. 435/108, 252.3, 435/252.31, 252.5

(56) References Cited

U.S. PATENT DOCUMENTS 4,824,786 A * 4/1989 Hanson et al. ............ 435/252.3

FOREIGN PATENT DOCUMENTS

| EP | 0 035 831 | 9/1981 |
| GB | 2 194 247 | 3/1988 |
| JP | 61 128897 | 5/1986 |
| WO | 00 61723 | 10/2000 |

OTHER PUBLICATIONS

DSMZ Catalog, #DMS–5898, Jan. 2001.*
DSMZ Catalog, #DMS–6813, Jan. 2001.*
Egorova T. A. Et Al: "Isolation of individual amino acids from various microbiological sources using reversed–phase high–performance liquidchromatography" Journal of Chromatography B: Biomedical Applications, NL, Elsevier Science Publishers, vol. 665, No. 1, Mar. 10, 1995, pp. 53–62, XP004043628 ISSN: 0378–4347 *the whole document*.

Database WPI, Section Ch, Week 198630, Derwent Publications Ltd., London, GB; Class B05, AN 1986–194624 XP002172586 & JP 61 128897 A (Ajinomoto KK), Jun. 16, 1986 *abstract*.

Database Biosis Online! Biosciences Information Service, Philadelphia, PA, US; 1990 Maksimova N P Et Al: "Regulation of Phenylalanine Biosynthesis in an Obligate Methylotroph Methylobacillus M75" Database accession No. PREV199191134485 XP002172585 *abstract* & Molekulyarnaya Genetika Mikrobiologiya I Virusologiya, No. 10, 1990, pp. 28–30, ISSN: 0208–0613.

Kearney P Et Al: "Regulation and Routes of Biosynthesis of Serine and Arginine in Methylophilus–Methylotrophus AS1" FEMS (Federation of European Microbiological Societies) Microbiology, vol. 42, No. 2–3, 1987, pp. 109–112, XP002929567, 1987, ISSN: 0378–1087.

* cited by examiner

*Primary Examiner*—Christopher R. Tate
*Assistant Examiner*—Randall Winston
(74) *Attorney, Agent, or Firm*—Oblon, Spivak, McClelland, Maier & Neustadt, P.C.

(57) ABSTRACT

A method for producing L-phenylalanine, comprising the steps of:

culturing a bacterium belonging to the genus Methylophilus which has an ability to produce L-phenylalanine and is resistant to a phenylalanine analog, in a culture medium to produce and accumulate L-phenylalanine in a culture, and recovering L-phenylalanine from the culture.

8 Claims, No Drawings

METHOD FOR PRODUCING L-PHENYLALANINE

BACKGROUND OF THE INVENTION

The present invention relates to a method for producing L-phenylalanine, in particular, to a bacterium belonging to the genus Methylophilus and having an ability to produce L-phenylalanine and a method for producing L-phenylalanine using a bacterium belonging to the genus Methylophilus.

As a method for producing L-phenylalanine by using a microorganism by fermentation, those using recombinant bacteria belonging to the genus Escherichia (Japanese Patent Application Laid-Open Nos. 56-1890, 57-170184, 58-103398, 61-92565 and 1-104160, and International Publication No. WO 87/00202) are known. As a method for producing L-phenylalanine or L-tyrosine, one using a mutant belonging to the genus Corynebacterium (Japanese Patent Application Laid-Open No. 61-128897), and those using recombinant bacteria belonging to the genus Corynebacterium (Japanese Patent Application Laid-Open Nos. 60-34197, 60-24192, 61-260892, and 61-124375) are known.

However, production of L-phenylalanine by using a bacterium belonging to the genus Methylophilus is not known.

SUMMARY OF THE INVENTION

An object of the present invention is to provide a bacterium having an ability to produce L-phenylalanine and a method for producing L-phenylalanine by using the bacterium.

The present inventors have found that a bacterium belonging to the genus Methylophilus which is resistant to a phenylalanine analog, has a high ability to produce L-phenylalanine. Based on the finding, the present invention has been accomplished.

The present invention provides a bacterium belonging to the genus Methylophilus, which has an ability to produce L-phenylalanine and is resistant to a phenylalanine analog (hereinafter, also referred to as "bacterium of the present invention").

The bacterium of the present invention is preferably resistant to the phenylalanine analog and L-phenylalanine.

The bacterium of the present invention is preferably resistant to DL-p-fluorophenylalanine.

The bacterium of the present invention is preferably obtained by selecting a strain which is resistant to the phenylalanine analog and L-phenylalanine from bacteria belonging to the genus Methylophilus, wherein said selection is performed at least once for each of the phenylalanine analog and L-phenylalanine in any order.

The bacterium of the present invention is more preferably resistant to DL-p-fluorophenylalanine and m-fluorophenylalanine, as well as to L-phenylalanine.

The bacterium of the present invention is more preferably obtained by selecting a strain which is resistant to DL-p-fluorophenylalanine, m-fluorophenylalanine and L-phenylalanine from bacteria belonging to the genus Methylophilus, wherein said selection is performed at least once for each of DL-p-fluorophenylalanine, m-fluorophenylalanine and L-phenylalanine in any order.

The bacterium of the present invention is preferably resistant to DL-p-fluorophenylalanine, m-fluorophenylalanine and cinnamic acid, as well as L-phenylalanine.

The bacterium of the present invention is more preferably obtained by selecting a strain which is resistant to DL-p-fluorophenylalanine, m-fluorophenylalanine, cinnamic acid and L-phenylalanine from bacteria belonging to the genus Methylophilus, wherein said selection is performed at least once for each of DL-p-fluorophenylalanine, m-fluorophenylalanine, cinnamic acid and L-phenylalanine in any order.

The bacterium of the present invention is preferably *Methylophilus methylotrophus*.

The present invention also provides a method for producing L-phenylalanine, comprising the steps of:

culturing the bacterium of the present invention in a culture medium to produce and accumulate L-phenylalanine in a culture, and recovering L-phenylalanine from the culture (hereinafter, also referred to as "method of the present invention).

DETAILED DESCRIPTION OF THE INVENTION

<1> The Bacterium of the Present Invention

The bacterium of the present invention is a bacterium belonging to the genus Methylophilus, which has an ability to produce L-phenylalanine and is resistant to a phenylalanine analog, and preferably to the phenylalanine analog and L-phenylalanine.

The bacterium belonging to the genus Methylophilus includes *Methylophilus methylotrophus*.

The ability to produce L-phenylalanine means an ability to accumulate a significant amount of L-phenylalanine in a medium when the bacterium is cultured in the medium. Usually, it means an ability to accumulate not less than 0.5 g/l of L-phenylalanine under the conditions described in Examples mentioned below.

Examples of the phenylalanine analog are DL-p-fluorophenylalanine, m-fluorophenylalanine, β-amino-β-phenylpropionic acid, o-fluorophenylalanine, β-2-thienylalanine, β-3-thienylalanine, β-2-furylalanine, β-3-furylalanine, o-aminophenylalanine, p-aminophenylalanine, m-aminophenylalanine, α-amino-β-phenylethanesulfonate, β-2-pyrrolalanine, 1-cyclopentene-1-alanine, 1-cyclohexene-1-alanine, β-4-pyridylalanine, β-4-pyrazolylalanine, p-nitro-phenylalanine, cyclohexylalanine, o-chlorophenylalanine, m-chlorophenylalanine, p-chlorophenylalanine, o-bromophenylalanine, m-bromophenylalanine, p-bromophenylalanine, β-4-thiazolealanine and the like.

To be resistant to an phenylalanine analog means that the bacterium can grow in the presence of the phenylalanine analog in the amount at which the wild type strain (for example, strain AS-1) can not grow. The amount varies depending on the kinds of the phenylalanine analog. In the case of DL-p-fluorophenylalanine, it is usually 2 g/l under the conditions described in Examples mentioned below, and in the case of m-fluorophenylalanine, it is usually 1 g/l under the conditions described in Examples mentioned below.

It is preferred that the bacterium of the present invention is resistant to at least two kinds of the phenylalanine analog. For example, it is preferred that it is resistant to DL-p-fluorophenylalanine and m-fluorophenylalanine.

To be resistant to L-phenylalanine means that the bacterium can grow in the presence of L-phenylalanine in the amount at which the wild type strain (for example, strain AS-1) can not grow. The amount is usually 8 g/l under the conditions described in Examples mentioned below.

The bacterium of the present invention is preferably resistant to a higher concentration (for example, 0.1 M) of L-phenylalanine.

The bacterium of the present invention can be obtained by conferring the required resistances to a bacterium belonging to the genus Methylophilus in order. The order of conferring the phenylalanine analog resistance and the L-phenylalanine resistance is not limited and the conferring may be made in any order.

The method of obtaining a bacterium belonging to the genus Methylophilus which is resistant to the phenylalanine analog and a bacterium belonging to the genus Methylophilus which is resistant to L-phenylalanine will be explained below.

The bacteria belonging to the genus Methylophilus which is resistant to a phenylalanine analog can be obtained by culturing bacteria belonging to the genus Methylophilus in a minimal medium containing the phenylalanine analog at the growth inhibitory concentration and selecting a growing strain.

The selection of the phenylalanine-analog-resistant strain may be performed with one kind of the phenylalanine analog, or with more kinds of the phenylalanine analogs. The selection of the strain may be performed once or more for one kind of the phenylalanine analog.

An amount of the phenylalanine analog which is to be added to the medium depends on a kind of the phenylalanine analog, but is preferably not less than 2 g/L in the case of DL-p-fluorophenylalanine. The bacteria belonging to the genus Methylophilus may be subjected to a mutation treatment prior to the selection. Mutation may be performed by ultraviolet irradiation or by treatment with a mutagen usually used for artificial mutagenesis such as N-methyl-N'-nitro-N-nitrosoguanidine (NTG) or nitrous acid and the like.

The bacteria belonging to the genus Methylophilus which is resistant to L-phenylalanine can be obtained by culturing bacteria belonging to the genus Methylophilus in a minimal medium containing L-phenylalanine at the concentration that causes growth inhibition, and selecting a growing strain. Growth inhibition herein refers to slow growth or stop of growth. The selection of the strains may be performed once or more. A concentration of L-phenylalanine in the medium is not particularly limited, but it is exemplified by not less than 0.05 M, preferably 0.1 M. The bacteria belonging to the genus Methylophilus may be subjected to a mutation treatment prior to the selection in the same manner as described above.

The bacterium belonging to the genus Methylophilus which is resistant to L-phenylalanine, obtained as mentioned above, can grow in the presence of L-phenylalanine at a concentration at which its parent strain can not grow.

The bacterium of the present invention is preferably resistant to cinnamic acid.

To be resistant to cinnamic acid means that the bacterium can grow in the presence of cinnamic acid in the amount at which the wild type strain (for example, strain AS-1) can not grow. The amount is usually 50 mg/l under the conditions described in Examples mentioned below.

The bacteria belonging to the genus Methylophilus which is resistant to cinnamic acid can be obtained by a similar way to that for phenylalanine analog-resistant bacteria. The order of conferring the cinnamic acid resistance, the phenylalanine analog resistance and the L-phenylalanine resistance is not limited and the conferring may be made in any order.

L-Phenylalanine is concerned with several regulation steps on L-phenylalanine biosynthesis. Therefore, single mutation which causes L-phenylalanine resistance may be effective for improvement of L-phenylalanine productivity, however, it is preferably that more regulations are desensitized by double or more mutations. A bacterium belonging to the genus Methylophilus which has single mutation can be used as a starting source for breeding of an L-phenylalanine-producing strain, even though its productivity of L-phenylalanine is low.

The bacterium of the present invention may be enhanced in activity of one or more enzymes of L-phenylalanine biosynthetic pathway by usual mutation treatment or genetic engineering techniques.

For example, L-phenylalanine biosynthesis can be enhanced by increasing an ability to produce phosphoenol pyruvate in a bacterium belonging to the genus Methylophilus (International Publication No. WO 97/08333).

L-Phenylalanine productivity is improved by enhancing a desensitized chorismate mutase-prephenate dehydratase gene (Japanese Patent Application Laid-Open Nos. 5-236947 and 62-130693), and/or a desensitized 3-deoxyl-D-arabino-hepturosonic acid 7-phosphate synthase gene (Japanese Patent Application Laid-Open Nos. 5-236947 and 61-124375).

<2> The Method of the Present Invention

The method of the present invention is a method for producing L-phenylalanine comprising cultivating the bacterium of the present invention in a culture medium, to produce and accumulate L-phenylalanine in a culture, and recovering L-phenylalanine from the culture.

The cultivation of the bacterium of the present invention may be performed by the method which is usually used for cultivation of methanol-assimilating microorganisms. The culture medium used in the present invention may be either a synthetic medium or a natural medium, so long as the medium includes a carbon source, a nitrogen source and mineral nutrients and, if necessary, other organic micronutrients.

If methanol is used as a main carbon source, L-phenylalanine can be produced inexpensively. Methanol is usually added to the culture medium usually in amount of 0.001 to 30% by weight, when it is used as a main carbon source. As the nitrogen source, ammonium sulfate may be used by adding it to the culture medium. In addition to these, a small amount of mineral nutrients such as potassium phosphate, sodium phosphate, magnesium sulfate, ferrous sulfate, and manganese sulfate may be used.

The cultivation is performed usually under aerobic conditions such as shaking culture and aeration and stirring culture, at pH of 5 to 9, and at a temperature of 20 to 40° C. It is usually completed for 24 to 120 hours.

The culture includes cells and the culture medium, and is preferably the culture medium.

The recover of L-phenylalanine from the culture may be performed according to combination of known methods such as ionexchange resin method and precipitation method.

EXAMPLES

The present invention is described in details in reference to examples. Methods for cultivation of *Methylophilus methylotrophus* and for analysis of L-phenylalanine which were used in the following examples are as follows:

<1> Cultivation in Tubes

1. Seed Culture

The strain was grown on plates or slants with 121(Fe2)-medium agar containing 1% methanol at 30° C. for 48–72 hours. And then the strain was inoculated into 5 ml 121 (Fe2)-medium containing 2% methanol used as the seed medium in tubes with capacity of 40 ml. The seed culture was incubated on a rotary shaker at 37° C. for 18 hours.

2. Fermentation in Tubes

The cultivation of L-phenylalanine producer was carried out at 37° C. in 5 ml of 121(Fe2)-medium containing 2% methanol and 3% calcium carbonate in tubes with capacity of 40 ml. Twenty four hours after the start of cultivation, the another portion of 2% methanol was added and the cultivation was continued for further 48 hours at 37° C. on a rotary shaker.

The composition of 121(Fe2)-medium containing 2% methanol and 3% calcium carbonate (1 liter):

| | | |
|---|---|---|
| $K_2HPO_4.3H_2O$ | 1.57 | g |
| $KH_2PO_4$ | 0.62 | g |
| $(NH_4)_2SO_4$ | 3 | g |
| NaCl | 0.1 | g |
| $MgSO_4.7H_2O$ | 0.2 | g |
| $CaCl_2$ | 0.025 | g |
| $EDTA-Na_2$ | 5 | mg |
| $FeSO_4.7H_2O$ | 3 | mg |
| $MnSO_4.5H_2O$ | 0.01 | mg |
| $ZnSO_4.7H_2O$ | 0.07 | mg |
| $Na_2MoO_4.2H_2O$ | 0.01 | mg |
| $H_3BO_3$ | 0.01 | mg |
| $CoCl_2.6H_2O$ | 0.005 | mg |
| $CuSO_4.5H_2O$ | 0.005 | mg |
| Methanol | 20 | ml |
| | (filter sterilized) | |
| $CaCO_3$ | 30 | g |
| pH | 7.0 | |

Initial volume of medium in fermentation tubes: 5 ml.
Inoculum size: 10%.
Temperature: 37° C.
Agitation: 250 rpm on shaker.

<2> Analysis of L-phenylalanine in Fermentation Broth
1. Sample Preparation

The samples of fermentation broth were centrifuged 15 min on model 5415C microfuge (Eppendorf) with the aim to remove cells and debris. Supernatant was used for high performance liquid chromatography (HPLC) analysis.

2. Chromatographic Determination of L-phenylalanine

The chromatographic system consisted of a HPLC pump model 30 (Gilson), and model 2151 variable wavelength monitor operated at 245 nm (LKB). Samples were injected using model 7410 injector with 1 μl internal sample loop (Rheodyne). Column was thermostated with laboratory made water-jacketed thermostat at 45° C.

Glass cartridge system with 150 mm×3.9 mm I.D. glass cartridges packed with 5 μm Separon C18 sorbent (Tessek) was used for all separations. Eluent consisted of 0.001 M $CuSO_4$ in water/acetonitril (80/20(v/v)).

Samples of fermentation broth were centrifuged for 5 min at 13,000×g and injected without further preparation.

The data were processed using an IBM PC/AT compatible data station with model 960 Interface and Nelson PC Integrator software (PE Nelson). Peaks were calculated using external standard technique.

Example 1

Construction of *Methylophilus methylotrophus* Mutant Strains which Have Ability to Produce L-phenylalanine <1> Mutagenesis and Selection of Mutants Resistant to DL-p-fluorophenylalanine, Aromatic Amino Acid Analog The *Methylophilus methylotrophus* AS-1 (NCIB 10515; ATCC 53528) strain was tested for the sensivity to the DL-p-fluorophenylalanine, an aromatic amino acid analog. The sensivity has been tested on 121(Fe2)-agar medium containing different concentrations of DL-p-fluorophenylalanine. The $10^8$ c.f.u./ml of *M. methylotrophus* bacteria were plated and grown at +30° C. for 3 days. The 1 mg/ml of the DL-p-fluorophenylalanine totally inhibited the growth of the bacteria lawn. To select the analog-resistant mutants, the $10^8$ bacteria of *M. methylotrophus* strain was seeded on plates carrying 2 mg/ml of DL-p-fluorophenylalanine. The several crystals of N-methyl-N'-nitro-N-nitrosoguanidin (hereinafter abbreviated to NG) mutagen was placed in the middle of the plate. After 4–5 days at 30° C., the plates were analyzed. The bacteria did not show growth near NG mutagen, but at 3–4 cm from it, the analog resistant mutant colonies grew. The big colonies were picked up and purified on the same media with analog DL-p-fluorophenylalanine. The *M. methylotrophus* DL-p-fluorophenylalanine resistant (hereinafter abbreviated to $pFp^R$) mutants were cultivated and concentration of L-phenylalanine in the fermentation medium was measured as described above. The best *M. methylotrophus* $pFp^R$ mutant No. 227 produced 30 mg/L of L-phenylalanine, near 1 g/L of L-valine, and 0.2 g/L of L-leucine, L-isoleucine and L-alanine. The thin layer chromatography approved HPLC analysis results.

<2> Mutagenesis and Selection of the *Methylophilus methylotrophus* Mutants Resistant to the High Concentrations of L-phenylalanine in the Growing Medium The *Methylophilus methylotrophus* DL-p-fluorophenylalanine resistant mutants produced L-phenylalanine but was sensitive to the high concentrations of L-phenylalanine if it was presented in the medium. The 0.1 M of L-phenylalanine totally inhibited the growth of the *M. methylotrophus* $pFp^R$ mutant No. 227 if it was added into the agarized 121-medium.

In order to eliminate this sensitivity and to increase strains productivity, the mutants resistant to the higher concentrations of L-phenylalanine presented in growing medium were selected. As a parental strain for the selection of the L-phenylalanine resistant mutants (hereinafter abbreviated to $phe^R$), the *M. methylotrophus* No. 227 ($pFp^R$ mutant strain) producing a little amount (30 mg/l) of L-phenylalanine was used. The selection medium was the 121(Fe2)-agar medium with 1% methanol and 0.05 M L-phenylalanine. The mutagenesis by NG was performed as it was described above. The L-phenylalanine resistant mutant colonies were several times purified on the same medium and later on medium without 0.05 M of L-phenylalanine. The $phe^R$-marker in mutants was stable inherited and not lost without selection pressure. The selected *M. methylotrophus* $pFp^R$ $phe^R$ mutants were cultivated and the concentration of L-phenylalanine in the fermentation medium was measured as described above. The best *M. methylotrophus* $pFp^R$ $phe^R$ mutant No. 227-16 carrying the mutation of the resistance to the high L-phenylalanine concentrations produced 0.4 g/l of L-phenylalanine. Thus, the $phe^R$-mutation, as the second mutation in *M. methylotrophus* $pFp^R$ $phe^R$ mutant No. 227-16, elevated the L-phenylalanine production more than 10 times: the $pFp^R$-mutant (No. 227) produced 30 mg/l of L-phenylalanine and the double $pFp^R$ $phe^R$-mutant (No. 227-16) produced 400 mg/l of L-phenylalanine.

It was found that the *Methylophilus methylotrophus* $pFp^R$ $phe^R$ mutant strain No. 227-16 was also resistant to a 0.5 g/l meta-fluorophenylalanine besides resistance to 2 g/l of DL-p-fluorophenylalanine and to 0.05 M of L-phenylalanine. However, strain No. 227-16 showed only a slight growth on 1 g/l of meta-fluorophenylalanine. The new mutants which were resistant to 1 g/L of meta-fluorophenylalanine (hereinafter abbreviated to $mFp^R$) were isolated from the strain No. 227-16 after NG-mutagenesis as it was described above. The resulted new *M. methylotrophus* $pFp^R$ $phe^R$ $mFp^R$ mutant strain No. 227-16-10, produced the same quantity of L-phenylalanine as its predecessor (0.4 g/l).

A new *M. methylotrophus* pFp$^R$ phe$^R$ mFp$^R$ phe$^{RR}$ mutant strain No. 227-16-10-11, which was resistant to the higher concentrations of L-phenylalanine (0.1 M) (hereinafter abbreviated to phe$^{RR}$), was isolated from the strain No. 227-16-10 after NG-mutagenesis as it was described above. The phe$^{RR}$-mutant strain produced in tubes 0.5–0.7 g/l L-phenylalanine, 0.3 g/l L-valine, 0.2 g/l L-leucine and less than 0.1 g/l of L-isoleucine, L-alanine and L-glutamic acid.

The new *M. methylotrophus* pFp$^R$-phe$^R$-mFp$^R$-phe$^{RR}$-cin$^R$ mutant strain No. 227-16-10-11-cin8, which was resistant to cinnamic acid (50 mg/L), the chemical structure analog of L-phenylalanine, (hereinafter abbreviated to cin$^R$) was isolated from a No. 227-16-10-11 strain after NG-mutagenesis as it was described above. The cin$^R$-mutant strain produced in tubes 0.8–0.9 g/l L-phenylalanine and 0.6 g/l L-valine.

The strains Nos. 227, 227-16, 227-16-10, 227-16-10-11 and 227-16-10-11-cin8 have been deposited in the Russian National Collection of Industrial Microorganisms (VKPM) on Feb. 10, 2000 (converted to a deposition according to the provisions of Budapest Treaty on Jul. 18, 2000) under the accession numbers VKPM B-7909, VKPM B-7910, VKPM B-7911, VKPM B-7912, and VKPM B-7913, respectively.

What is claimed is:

1. A biologically pure culture of a mutant strain of *Methylophilus methylotrophus* bacterium, which produces L-phenylalanine and is resistant to a phenylalanine analog and L-phenylalanine compared with a wild type strain.

2. The biologically pure culture of a mutant strain of *Methylophilus methylotrophus* bacterium according to claim 1, which is resistant to DL-p-fluorophenylalanine compared with a wild type strain.

3. The biologically pure culture of a mutant strain of *Methylophilus methylotrophus* bacterium according to claim 1, which is obtained by selecting a strain which is resistant to the phenylalanine analog and L-phenylalanine from bacteria belonging to *Methylophilus methylotrophus,* wherein said selection is performed at least once for each of the phenylalanine analog and L-phenylalanine in any order.

4. The biologically pure culture of a mutant strain of *Methylophilus methylotrophus* bacterium according to claim 1, which is resistant to DL-p-fluorophenylalanine and m-fluorophenylalanine compared with a wild type strain.

5. The biologically pure culture of a mutant strain of *Methylophilus methylotrophus* bacterium according to claim 4, which is obtained by selecting a strain which is resistant to DL-p-fluorophenylalanine, m-fluorophenylalanine and L-phenylalanine from bacteria belonging to *Methylophilus methylotrophus,* wherein said selection is performed at least once for each of DL-p-fluorophenylalanine, m-fluorophenylalanine and L-phenylalanine in any order.

6. The biologically pure culture of a mutant strain of *Methylophilus methylotrophus* bacterium according to claim 1, which is resistant to DL-p-fluorophenylalanine, m-fluorophenylalanine and cinnamic acid compared with a wild type strain.

7. The biologically pure culture of a mutant strain of *Methylophilus methylotrophus* bacterium according to claim 6, which is obtained by selecting a strain which is resistant to DL-p-fluorophenylalanine, m-fluorophenylalanine, cinnamic acid and L-phenylalanine from bacteria belonging to *Methylophilus methylotrophus,* wherein said selection is performed at least once for each of DL-p-fluorophenylalanine, m-fluorophenylalanine, cinnamic acid and L-phenylalanine in any order.

8. A method for producing L-phenylalanine, comprising the steps of:

culturing the biologically pure culture of a mutant strain of *Methylophilus methylotrophus* bacterium as defined in claim 1 in a culture medium to produce and accumulate L-phenylalanine in a culture, and recovering L-phenylalanine from the culture.

* * * * *